United States Patent [19]

Ito et al.

[11] 4,448,949
[45] May 15, 1984

[54] LATENT CURING AGENTS FOR EPOXY RESINS

[75] Inventors: Nobuo Ito, Oiso; Koji Takeuchi, Yokohama; Masahiro Abe; Kiyomiki Hirai, both of Kawasaki, all of Japan

[73] Assignee: General Electric Company, Mt. Vernon, Ind.

[21] Appl. No.: 516,332

[22] Filed: Jul. 22, 1983

[30] Foreign Application Priority Data

Jul. 30, 1982 [JP] Japan ................................ 57-134453

[51] Int. Cl.³ ............................................. C08G 59/44
[52] U.S. Cl. ...................................... 528/99; 525/504; 564/150
[58] Field of Search .......................... 528/99; 564/150; 525/504

[56] References Cited

U.S. PATENT DOCUMENTS

| 2,847,395 | 8/1958 | Wear | 528/123 X |
| 3,467,707 | 9/1969 | Aelony | 528/123 X |
| 3,530,173 | 9/1970 | Aelony | 528/99 X |

Primary Examiner—Earl A. Nielsen
Attorney, Agent, or Firm—Martin B. Barancik

[57] ABSTRACT

Hydrazides of the formula

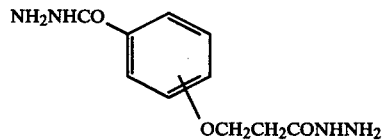

are good curing agents for epoxy resin. The curing agents are useful in formulating novel storable one-package, heat-curable epoxy resin-based compositions.

7 Claims, No Drawings

LATENT CURING AGENTS FOR EPOXY RESINS

The present invention relates to latent curing agents for epoxy resins.

Epoxy resins are widely employed as electric insulating materials, various moulded products, adhesives or coatings, because they give valuable cured resins having excellent mechanical, electrical and chemical properties when cured with suitable curing agents for example acid anhydride and amine curing agents. However, epoxy resin composition incorporating amine curing agents are cured rapidly at ordinary temperature and at elevated temperature and hence they lack storage stability. Also, epoxy resin composition incorporating acid anhydride curing agents are stable at ordinary temperature but heating for a long period of time at elevated temperature is required for full curing. Usually, tertiary amines, quaternary ammonium compounds or organo metal complexes are further added to the composition for purpose of accelerating curing rate. However, the addition of such cure accelerator impairs storage stability markedly.

There have been eagerly desired so-called latent curing agents which are compatible with epoxy resins to form composition which is stable at relatively low temperature and which is rapidly cured when heated to elevated temperature. Representative compounds which have been heretofore proposed as latent curing agents are dicyandiamide, dibasic acid hydrazide, boron trifluoride-amine adduct, guanamine and melamine. Among these compounds, dicyandiamide, dibasic acid hydrazide and quanamine are useful in formulating epoxy resin compositions having excellent storage stability but full curing by means of these compound could be achieved by heating at higher temperature than 150° C. for a long time. Also, boron trifluoride-amine adduct is hard to treat owing to its high hygroscopic property and it affects adversely upon the physical properties of the cured resin.

There has been heretofore known almost no latent epoxy curing agent which causes rapid curing at moderate elevated temperature, that is 100° C.–150° C. and which gives epoxy resin composition having excellent storage stability at ordinary temperature.

An object of the present invention is to provide novel hydrazide-type curing agents which are useful in making storable one-package curable epoxy resin compositions.

Another object of the present invention is to provide hydrazide-type curing agents which alone or together with other curing agents can activate a rapid curing of epoxy resin composition at relatively low temperatures and yet be extraordinarily resistant to gelling at 40° C. for three weeks or more weeks.

The above objects of the present invention may be substantially achieved by providing as curing agent hydrazide compound having the following formula.

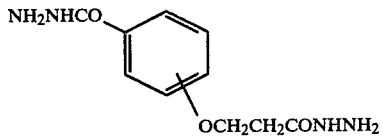

The hydrazides which may be represented by the above formula may be readily prepared, for example by reacting an equimolar adduct of alkyl m-, p- or o-hydroxybenzoate and acrylic ester, with hydrazine hydrate (Kobunshi Kagaku, Vol. 30, No. 333, pp. 51–55 (1973)).

The hitherto known dibasic acid hydrazides such as adipic acid hydrazide, sebacic acid hydrazide, isophthalic acid hydrazide and the like are high melting compound above 180° C. and the epoxy resin compositions incorporating such dibasic acid hydrazides is cured when heated to 150° C. or higher temperatures. Contrary thereto, the hydrazides of the present invention are relatively low melting compounds and provide when incorporated into an epoxy resin, curable composition which are stable for periods of several weeks at 40° C. and which can thereafter be readily cured at temperatures of as low as about 100°~130° C. to give colorless, transparent and tough cured product.

The required amount of curing agent is determined by the number of active hydrogen atoms in the curing agent employed and the number of epoxy groups in the epoxy resins. In general, 0.5–1.5 preferably 0.7–1.2 active hydrogen equivalent weight per epoxy equivalent weight is employed.

As epoxy resins which may be applied to the hydrazide curing agents of the present invention, various well-known ones having an average of more than 1 epoxy groups in the molecule may be employed. Representative epoxy resins are those based on glycidyl ethers of polyhydric phenols such as 2,2-bis(4-hydroxyphenyl)-propane (Bisphenol A), resorcinol, hydroquinone, pyrocatechol, saligenin, glycidyl ether of Bisphenol F and glycidyl ether of phenol-formaldehyde resin.

If necessary, other curing agents, cure accelerator and fillers may be employed in combination with the curing agent of the present invention.

The following examples illustrate the preparation of the hydrazides of the present invention.

EXAMPLE 1

Preparation of 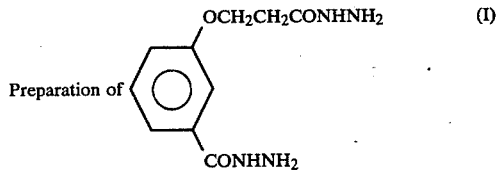

In an autoclave equipped with a magnetic stirrer were placed 20 g of methyl m-hydroxybenzoate, 56.4 g of methyl acrylate and 0.4 g of sodium methylate. After air therein was substituted with gaseous nitrogen, the mixture was heated at 100°–110° C. for 5 hours. After cooling, 200 ml of ethyl ether was added and the reaction mixture was washed twice with 100 ml of 3% aqueous sodium hydroxide and washed three times with 100 ml of water. The ethyl ether layer was concentrated to dryness whereby there was obtained 15.5 g of methyl m-hydroxybenzoate-methyl acrylate adduct (I)''

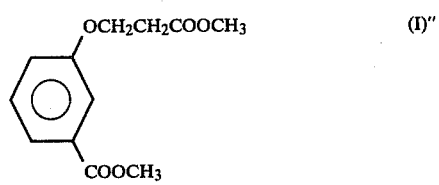

15 Grams of the adduct (I)″ and 15.75 g of hydrazine hydrate were dissolved in 100 ml of methanol in a 200 ml flask. The mixture was allowed to stand at room temperature for 70 hours. The precipitated crystals were filtered, washed with methanol and recrystallized from mixed solvent of 200 ml of methanol and 100 ml of water to obtain 4 g of the target product.

The analytical values were as shown below.

Melting point 163°~164° C.

| Elemental analysis | | | |
|---|---|---|---|
| | (%) | | |
| | C | H | N |
| Found | 50.05 | 6.23 | 22.93 |
| Calculated for C$_{10}$H$_{14}$N$_4$O$_3$ | 50.42 | 5.92 | 23.52 |

EXAMPLE 2

Preparation of NH$_2$NHCOCH$_2$CH$_2$O— 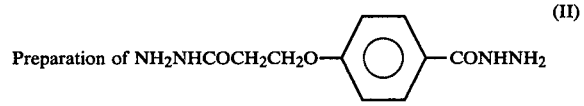 —CONHNH$_2$ (II)

The procedure of Example 1 was repeated using 20 g of methyl p-hydroxybenzoate in place of 20 g of methyl m-hydroxybenzoate to obtain 16.2 g of methyl p-hydroxybenzoate-methyl acrylate adduct (II)″ having the following structural formula CH$_3$OCOCH$_2$CH$_2$O— 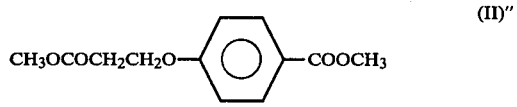 —COOCH$_3$ (II)″

16 Grams of the adduct was dissolved in 100 ml of methanol and then 16.5 g of hydrazine hydrate was added thereto. The mixture was refluxed for 4 hours. The reaction mixture was concentrated under reduced pressure to remove the unreacted hydrazine hydrate and methanol. The residue was dissolved in methanol and allowed to stand overnight. The precipitated crystals were filtered and washed with methanol to obtain 5.8 g of the target product.

The analytical values were as shown below.

Melting point 165°-166° C.

| Elemental analysis | | | |
|---|---|---|---|
| | (%) | | |
| | C | H | N |
| Found | 50.68 | 6.19 | 23.24 |
| Calculated for C$_{10}$H$_{14}$N$_4$O$_3$ | 50.42 | 5.92 | 23.52 |

EXAMPLE 3

Reactivity and storage stability of the formulated epoxy resin composition were evaluated.

1. Preparation of the sample

The formulation of the sample is shown in Table 1. The individual components were sufficiently mixed in a mortar.

2. Evaluation of the reactivity (1) Onset temperature and peak temperature were measured by differential thermal analysis (DTA)

Sample weight: about 10 mg
Standard material: α-Al$_2$O$_3$
Heating rate: 5° C./min.

(2) The sample was put into the Geer's oven maintained to 130° C. and the resulted cure resin was observed on its appearance.

3. Storage stability

The sample was put into the Geer oven set to 40° C. and the day required for the sample becoming non-fluidity was measured.

TABLE 1

| | Formulation No. | | | | |
|---|---|---|---|---|---|
| | 1 | 2 | 3 | 4 | 5 |
| Epon 828*[1] | 100 | 100 | 100 | 100 | 100 |
| Compound (I) | 31 | | | | |
| Compound (II) | | 31 | | | |
| Adipic dihydrazide | | | 23 | | |
| Isophthalic dihydrazide | | | | 26 | |
| Dicyandiamide | | | | | 8 |

*[1]A product of Shell Chemical Co. bisphenol A type epoxy resin having epoxy equivalent of 175-210.

The obtained results are shown in Table 2.

TABLE 2

| | | Item | | | |
|---|---|---|---|---|---|
| | | Reactivity | | | |
| | Formulation No. | Onset temp. (°C.) | Peak temp. (°C.) | Appearance of the sample (130° C. 1 hr) | Storage stability (40° C.) |
| The present invention | No. 1 | 147 | 163 | Stiff and transparent material | >3 weeks |
| | 2 | 148 | 170 | Stiff and transparent material | ″ |
| Control | 3 | 151 | 173 | not cured | ″ |
| | 4 | 158 | 192 | ″ | ″ |
| | 5 | 160 | 199 | ″ | >3 weeks (Partial separation occurred) |

The result of Table 2 shows that the latent curing agent for epoxy resin in this invention has excellent storage stability and reactivity. Especially, the reactivity of this agent is superior to the control agent.

What we claim is:

1. A curable, storage-stable epoxy resin composition comprising (a) an epoxy resin having an average of more than one epoxy group per molecule and (b) as curing agent a compound having the formula

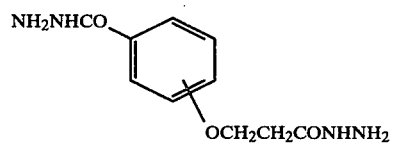

2. The curable epoxy resin composition claimed in claim 1, wherein the amount of said compound is enough to provide 0.5–1.5 times active hydrogen equivalent weight based on epoxy equivalent weight.

3. The curable epoxy resin composition claimed in claim 1, wherein said epoxy resin is polyglycidyl ether of polyhydric phenol.

4. A cured resin obtained by contacting an epoxy resin having an average of more than 1 epoxy group per molecule with as curing agent a compound having the formula

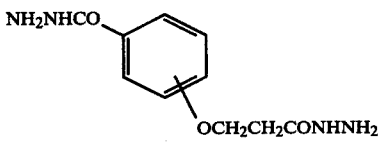

5. A process for curing an epoxy resin having an average of more than one epoxy group per molecule comprising (a) admixing with said epoxy resin a low temperature curing agent of the formula

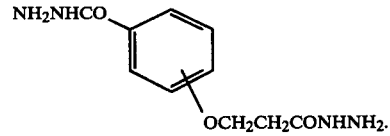

and (b) heating said epoxy resin composition at no greater than a temperature of 150° C.

6. The process according to claim 5, wherein said heating is conducted within a temperature range of from about 100° C. to about 130° C.

7. A low temperature epoxy resin curing agent consisting essentially of a compound having the formula NH$_2$NHCO—[benzene ring]—OCH$_2$CH$_2$CONHNH$_2$.

* * * * *

UNITED STATES PATENT AND TRADEMARK OFFICE
CERTIFICATE OF CORRECTION

PATENT NO. : 4,448,949

DATED : May 15, 1984

INVENTOR(S) : Ito, et. al.

It is certified that error appears in the above-identified patent and that said Letters Patent is hereby corrected as shown below:

On the Title page, item [73], Ajinomoto Company Incorporated, Tokyo, Japan--
and between item [56], and Abstract, insert Attorney, Agent, or Firm--
Oblon, Fisher, Spivak, McClelland & Maier, P.C.--

Signed and Sealed this

Twenty-fifth Day of May, 1993

Attest:

MICHAEL K. KIRK

Attesting Officer

Acting Commissioner of Patents and Trademarks